United States Patent [19]

Bertrand et al.

[11] Patent Number: 5,734,060
[45] Date of Patent: Mar. 31, 1998

[54] METHOD OF PREPARING ACYLISOCYANATES

[75] Inventors: Guy Bertrand, Pechbusque; Daniel Guyot, Montastruc la Conseillere; Michel Denarie, Pernes les Fontaines; Jean-Pierre Senet, Buthiers, all of France

[73] Assignee: Societe Nationale des Poudres et Explosifs, Paris Cedex, France

[21] Appl. No.: 715,725

[22] Filed: Sep. 19, 1996

[30] Foreign Application Priority Data

Oct. 5, 1995 [FR] France .................. 95 11722

[51] Int. Cl.$^6$ .................................. C07D 211/72
[52] U.S. Cl. .................. 546/316; 560/347; 560/340
[58] Field of Search .......................... 560/347, 340; 546/316

[56] References Cited

PUBLICATIONS

Database WPI, Week 7712, Derwent Publications Ltd., London, GB; AN 77–21324y XP002004594 & SU–A–498 290 (Tkachev A S), 14 Sep. 1976.

Chemical Abstracts, vol. 100, No. 7, 1984 Columbus, Ohio, US; abstract No. 51682q, XP002004593.

Zh. Obshch. Khim., vol. 53, No. 9, 1983, pp. 2155–2156, V.P. Kozyukov et al.

H. Hagemann: "Methoden Der Organischen Chemie (Houben–Weyl) Band E4, Kohlensaurederivate 1983, George Thieme Verlag, Stuttgart. New York XP002004592, p. 806–p. 808.

*Primary Examiner*—Samuel Barts
*Attorney, Agent, or Firm*—Bucknam and Archer

[57] ABSTRACT

The invention relates to a novel process for the preparation of acyl isocyanates which consists in reacting oxalyl chloride with an N-trialkylsilylcarboxamide or an N,N-bis (trialkylsilyl)carboxamide.

The process makes it possible to obtain acyl isocyanates in good yield, in particular acyl isocyanates derived from aliphatic amides, and under simplified reaction conditions.

11 Claims, No Drawings

METHOD OF PREPARING ACYLISOCYANATES

The present invention relates to a novel process for the preparation of acyl isocyanates using oxalyl chloride.

On account of their excellent reactivity, acyl isocyanates are very useful intermediates in the fields of agrochemistry and pharmacy, in particular for forming ureas and carbamates.

The first process for the preparation of acyl isocyanates consisted in reacting an acyl chloride with silver cyanate (J. Am. Chem. Soc. 62, 1595 (1940)). Unfortunately, this process cannot be used industrially on account of the high cost of silver cyanate.

According to another process, the silver cyanate is replaced by isocyanic acid (U.S. Pat. No. 3,155,700). However, this acid is very unstable and very difficult to prepare by decomposition of isocyanuric acid at a very high temperature such as 620° C.

From 1962 to 1965, A. J. Speziale et al. developed a process for the preparation of acyl isocyanates in which amides are reacted with oxalyl chloride (J. Org. Chem., 27, 3742 (1962), 28, 1805 (1963), 30, 4306 (1965)). Unfortunately, this process gives results which are very variable depending on the starting amides used; in particular the yields of acyl isocyanates from light primary or secondary aliphatic amides not substituted on the s-carbon with an electron-withdrawing group are very low. Furthermore, the large amount of hydrochloric acid formed at the same time as the isocyanates damages the plants and prevents the production of isocyanates which are sensitive to acidic conditions.

The subject of the present invention is a process for the preparation of acyl isocyanates, this being a process which does not have the drawbacks of the prior processes and which allows the production of a wide variety of acyl isocyanates under simplified reaction conditions.

According to the present invention, the process for the preparation of acyl isocyanates is characterized in that oxalyl chloride is reacted with an N-trialkylsilylcarboxamide or an N,N-bis(trialkylsilyl)carboxamide.

The reaction scheme for the process is as follows:

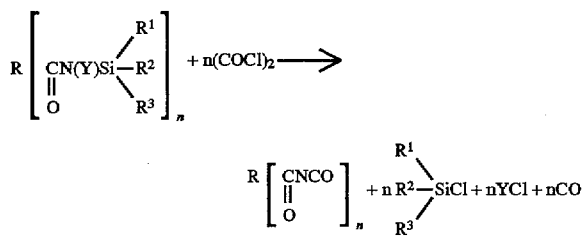

in which R represents the amide radical, $R^1$, $R^2$ and $R^3$, which may be identical or different, represent an alkyl radical, Y represents a hydrogen atom or a group

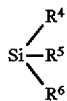

in which $R^4$, $R^5$ and $R^6$, which may be identical or different, represent an alkyl radical and n represents the number 1 or 2.

The process according to the invention allows the production of acyl isocyanates and in particular acyl isocyanates derived from aliphatic amides, in good yield. A trialkylchlorosilane is formed at the same time as the acyl isocyanate. This co-product may be recycled completely in order to prepare the starting silyl amide, which is a great advantage. Furthermore, hydrochloric acid is not released when the starting compound is a disilyl carboxamide and, when the carboxamide is monosilyl, the amount of hydrochloric acid which forms is less by half that released in the prior processes.

The N-trialkylsilylcarboxamides or the N,N-bis-(trialkylsilyl)carboxamides used as starting compounds are commercially available compounds or compounds which may be prepared very readily according to the process described by J. F. Klebe et al. in J. Am. Chem. Soc. (1966), 88, 3390-95, in particular by reaction of trialkylchlorosilanes with carboxamides.

The process according to the invention is suitable in particular for the conversion of the silyl carboxamides of formula

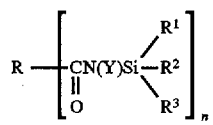

in which:

R represents a $C_1$ to $C_{20}$, preferably $C_1$ to $C_{10}$, saturated or unsaturated, substituted or unsubstituted, linear or branched aliphatic radical, a $C_4$ to $C_7$, saturated or unsaturated, substituted or unsubstituted cycloaliphatic radical, a substituted or unsubstituted phenyl, phenylene, naphthyl or naphthylene radical, a substituted or unsubstituted, preferably 5- or 6-membered, heteroaromatic radical, the hetero atom or atoms preferably being chosen from the group consisting of oxygen, nitrogen and sulphur atoms, $R^1$, $R^2$ and $R^3$, which may be identical or different, represent a $C_1$ to $C_4$ alkyl radical, Y represents a hydrogen atom or a group

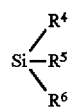

in which $R^4$, $R^5$ and $R^6$, which may be identical or different, represent a $C_1$ to $C_4$ alkyl radical and n represents the number 1 or 2.

The substituent(s) of R may be chosen in particular from the group consisting of halogen atoms, halogenated or non-halogenated aromatic or heteroaromatic groups and halogenated or non-halogenated alkoxy, preferably $C_1$ to $C_3$ alkoxy, or aryloxy groups, for example such as methoxy, phenyloxy and halophenyloxy. When R represents a cyclic radical, the substituents may also be chosen from halogenated or non-halogenated aliphatic radicals and the nitro group.

The halogen atoms are preferably chosen from chlorine, bromine and fluorine atoms.

When R represents a heteroaromatic radical, the hetero atom or atoms are more particularly nitrogen.

$R^1$, $R^2$, $R^3$, $R^4$, $R^5$ and $R^6$ preferably represent the methyl radical.

Among the acyl isocyanates which are obtained by the process according to the invention, mention may be made in particular of: acetyl, trichloroacetyl, phenylacetyl, methacryloyl, 3-ethoxy- or 3-methoxyacryloyl, hexanoyl, palmitoyl, stearoyl, isobutyryl, pivaloyl, cinnamoyl, cyclopentanecarbonyl, cyclohexanecarbonyl, benzoyl, 2,6-difluorobenzoyl, o-methoxybenzoyl, 2,6-dichlorobenzoyl, nitrobenzoyl, naphthoyl, nicotinoyl, chloronicotinoyl, 5-nitrofuroyl, malonyl, succinyl, adipoyl, terephthaloyl and fumaryl isocyanates.

The process may be carried out without solvent or with an organic solvent medium which is inert towards the compounds. When it is desired to prepare acyl isocyanates which are relatively unstable and sensitive to the reaction conditions such as the temperature, for example, it is preferred to carry out the reaction in a solvent medium. Among the inert solvents which are suitable, mention may be made of chlorinated or non-chlorinated aliphatic hydrocarbons, such as hexane, cyclohexane, heptane, dichloromethane and 1,2-dichloroethane, aromatic hydrocarbons such as toluene, chlorobenzene, di- and trichlorobenzene, oxide ethers such as diethyl ether, dioxane and tetrahydrofuran. The preferred solvents are chlorinated aliphatic hydrocarbons.

The silyl carboxamide and the oxalyl chloride are generally reacted in stoichiometric amount, but an excess of oxalyl chloride may also be used, such that the oxalyl chloride/carboxamide ratio is between 1 and 1.5. The carboxamide is usually added to the oxalyl chloride contained in the reactor.

The reaction temperature is generally between −15° C. and +120° C., and preferably between −15° C. and 100°C. During the phase of addition of the carboxamide, the reaction medium is preferably maintained at a low temperature, and the reaction is then often completed at a higher temperature, for example when a solvent is used, at the reflux temperature of the solvent.

When the side product obtained is trimethylchlorosilane, it is removed from the medium very easily given its low boiling point. The isocyanate may then be extracted easily, for example by distillation. When the isocyanate is relatively unstable, it is not separated from the solvent and the solution of the isocyanate in the solvent is used in order to carry out subsequent reactions for conversion of the isocyanate.

The acyl isocyanates are very useful for the preparation of many products in the fields of pharmacy, agrochemistry and polymers. Mention may be made, for example, of acetyl isocyanate used as a key intermediate in the preparation of triazolinones. Trichloroacetyl isocyanate is very widely used to form carbamate functions during the synthesis of antibiotics, in particular "cefuroxime". Methacryloyl isocyanate, which is very reactive, makes it possible, via copolymerization, to obtain materials which can be used for crosslinkable coatings, for dental adhesives or for acrylic elastomers. Novel drugs such as lipoxygenase inhibitors are prepared from benzoyl isocyanate. Substituted benzoyl isocyanates such as 2,6-difluorobenzoyl isocyanate are very widely used to manufacture many benzoylurea insecticides.

The examples which follow are intended to illustrate the present invention without, however, limiting it.

EXAMPLE 1

Preparation of hexanoyl isocyanate starting from N,N-bis(trimethylsilyl)hexanamide

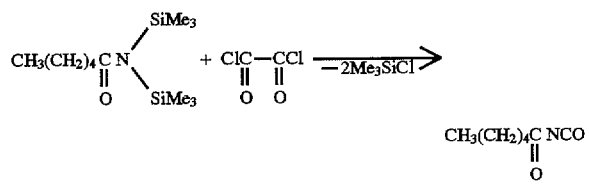

A solution of 1.5 g (11.80 mmol) of oxalyl chloride in 80 ml of 1,2-dichloroethane (1,2-DCE) is introduced into a 250 ml 2-necked round-bottomed flask fitted with condenser. The solution is cooled to 0° C. with an ice bath and 3.3 g (11.6 mmol) of pure N,N-bis(trimethylsilyl)hexanamide are added dropwise over 20 minutes with stirring. The reaction mixture turns a light yellow colour and remains homogeneous.

The reaction is completed by heating the mixture to the reflux temperature of the 1,2-DCE for 2 hours. The solvent and the trimethylchlorosilane formed are removed by distillation at normal pressure until the volume remaining is about 10 ml, then distillation under reduced pressure is carried out. 0.98 g (yield: 60%) of the expected isocyanate is obtained, this product having the following characteristics:

Very air-sensitive colourless liquid.

Boiling point (b.p.): 40° C./5·10$^{-2}$ mm Hg.

IR (CDCl$_3$):

1730 cm$^{-1}$ (C=O), 2240 cm$^{-1}$ (NCO) 2880 cm$^{-1}$, 2940 cm$^{-1}$ and 2960 cm$^{-1}$ (CH).

1H NMR(CDCl$_3$):

Complex multiplets centred on:

+0.9 ppm (m, 3H), +1.4 ppm (m, 6H), +2.4 ppm (m, 2H).

EXAMPLE 2

Preparation of hexanoyl isocyanate starting from N-trimethylsilylhexanamide

A solution of 4.34 g (34.17 mmol) of oxalyl chloride in 150 ml of 1,2-DCE is introduced into a 250 ml two-necked round-bottomed flask fitted with a condenser. The solution is cooled to 0° C. and a solution of 6.39 g (34.17 mmol) of N-trimethylsilylhexanamide dissolved in 30 ml of 1,2-DCE is added dropwise over 30 minutes with stirring. A white precipitate forms. This disappears as soon as the temperature returns to room temperature.

The reaction is completed by heating the reaction mixture at the reflux temperature of the solvent for 1 hour. After cooling to room temperature, a clear, pale yellow solution is obtained.

The solvent and the trimethylchlorosilane formed are removed by distillation at normal pressure until the residual volume is about 10 ml, then distillation under reduced pressure is carried out. 2.70 g (yield: 56%) of the expected isocyanate are obtained, this product having the following characteristics:

b.p.: 69°–70° C./20 mm Hg.

IR (CDCl$_3$):

1740 cm$^{-1}$ (CO), 2250 cm$^{-1}$ (NCO), 2900 cm$^{-1}$ (CH).

EXAMPLE 3

Preparation of benzoyl isocyanate starting from N,N-bis(trimethysilyl)benzamide

A solution of 1.27 g (10 mmol) of oxalyl chloride in 40 ml of 1,2-DCE is introduced into a 250 ml two-necked round-bottomed flask fitted with a condenser. The solution is cooled to 0° C. and 2.47 g (9.3 mmol) of pure N,N-bis(trimethylsilyl)benzamide are added dropwise over 15 min. The colour of the reaction mixture turns to yellow and a white precipitate forms. After heating the reaction medium for 1 hour at the reflux temperature of the 1,2-DCE, the starting disilyl amide is completely consumed (IR control). The solution is clear and brown in colour.

The solvent and the trimethylchlorosilane formed are collected in a trap at −196° C. by evaporation under vacuum (40° C./50 mm Hg). When the residual volume is about 3 ml, the crude product is transferred into a distillation flask and distillation is carried out at reduced pressure. 1.03 g (yield: 75%) of benzoyl isocyanate are obtained, this product having the following characteristics:

Air-sensitive colourless liquid.
b.p.:
125° C./50 mm
IR(1,2-DCE):
1600 cm$^{-1}$ (aromatic),
1700 cm$^{-1}$ (CO), 2250 cm$^{-1}$ (NCO).
$^{13}$C NMR (CDCl$_3$):
+128.688 ppm (s, meta C),
+230.398 ppm (s, ortho C),
+134.542 ppm (s, para C),
+164.884 ppm (s, C=0).

The trimethylchlorosilane recovered is assayed by $^1$H NMR relative to benzene taken as reference. The yield is 84.3% relative to the theoretical amount expected.

EXAMPLE 4

Preparation of benzoyl isocyanate starting from N-trimethylsilylbenzamide

A solution of 2.54 g (20 mmol) of oxalyl chloride in 90 ml of 1,2-DCE is introduced into a 250 ml two-necked round-bottomed flask fitted with a condenser. The solution is cooled to 0° C. and a solution of 3.86 (20 mmol) of N-trimethylsilylbenzamide dissolved in 30 ml of 1,2-DCE is added dropwise over 30 min. A white precipitate forms, which disappears when the reaction mixture returns to room temperature. The reaction is completed by heating the mixture at the reflux temperature of the 1,2-DCE for one hour. The colour of the solution is pale yellow, and there is no precipitate.

The process is then carried out as in the above example. The solvent and the trimethylchlorosilane formed are collected. The remaining brown liquid is then distilled under reduced pressure. 1.76 g (yield: 60%) of benzoyl isocyanate are obtained, this product having the following characteristics:

Very air-sensitive pale yellow liquid.
b.p.:
95-98° C./20 mm Hg.
IR (CDCl$_3$):
1600 cm$^{-1}$ (aromatic),
1700 cm$^{-1}$ (CO),
2250 cm$^{-1}$ (NCO).

EXAMPLE 5

Preparation of 2,6-difluorobenzoyl isocyanate

A solution of 0.46 g (3.6 mmol) of oxalyl chloride in 20 ml of 1,2-DCE is introduced into a 50 ml round-bottomed flask. 1 g (3.3 mmol) of pure N,N-bis(trimethylsilyl)-2,6-difluorobenzamide is added dropwise with stirring. The solution turns yellow. The reaction is immediate. The isocyanate formed and the residual oxalyl chloride are identified by IR spectrometry. The light products are evaporated off at 0.8 mm Hg and at room temperature.

0.40 g (yield:67%) of the expected isocyanate is obtained by distillation at 36° C./0.8 mm Hg.

EXAMPLE 6

Preparation of acetyl isocyanate

A solution of 0.62 g (4.88 mmol) of oxalyl chloride in 20 ml of 1,2-DCE is introduced into a 100 ml round-bottomed flask fitted with a condenser. The solution is cooled to 0° C. and 1 g (4.88 mmol) of N,N-bis(trimethylsilyl)acetamide is added dropwise over 10 min. The mixture turns pale yellow and becomes slightly cloudy. The reaction is completed by heating the mixture at the reflux temperature of the 1,2-DCE for 1 hour. The reaction mixture turns a dark brown colour.

The acetyl isocyanate obtained is not separated from the solvent, but is converted into carbamate, by adding 0.36 g (4.88 mmol) of tert-butanol to the medium. 0.39 g (yield: 50%) of CH$_3$—C(O)—NH—C(O)—O—C(CH$_3$)$_3$ is obtained, which product is characterized by $^1$H NMR and IR analysis.

EXAMPLE 7

Preparation of nicotinoyl isocyanate

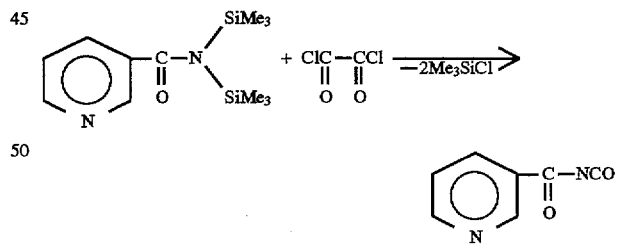

A solution of 1.91 g (15 mmol) of oxalyl chloride in 100 ml of 1,2-DCE is introduced into a 250 ml two-necked round-bottomed flask fitted with a condenser. The solution is cooled to 0° C. and 3.99 g (15 mmol) of pure N,N-bis(trimethylsilyl)nicotinamide are added dropwise over 15 min. A white precipitate forms and the solution turns a pale yellow colour. The reaction mixture is heated at the reflux temperature of the 1,2-DCE for one hour.

The stoichiometric amount, relative to the starting silyl nicotinamide, of tert-butanol is added to the reaction mixture and the carbamate

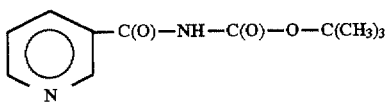

is obtained, which product characterized by $^1$H NMR and IR analysis, in a yield of 30%.

EXAMPLE 8

Preparation of 2-chloronicotinoyl isocyanate

A solution of 1.91 g (15 mmol) of oxalyl chloride in 100 ml of 1,2-DCE is introduced into a 250 ml two-necked round-bottomed flask fitted with a condenser. The solution is cooled to 0° C. and 4.50 g (15 mmol) of N,N-bis (trimethylsilyl)-2-chloronicotinamide are added dropwise over 15 min. The solution turns a pale yellow colour. After 15 min at 0° C., IR analysis carried out on a sample of the reaction medium shows considerable formation of the isocyanate: CO band at 1720 cm$^{-1}$ and NCO band at 2250 cm$^{-1}$.

The stoichiometric amount, relative to the starting silyl chloronicotinamide, of tert-butanol is added to the reaction medium. The carbamate

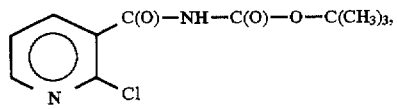

is obtained, which product characterized by $^1$H NMR and IR analysis, in a yield of 96%.

EXAMPLE 9

Preparation of methacryloyl isocyanate 29.8 g (130mmol) of N,N-bis(trimethylsilyl) methacrylamide in 250 ml of 1,2-DCE is introduced, under a nitrogen atmosphere, into a 500 ml two-necked round-bottomed flask fitted with a condenser. 16.5 g of oxalyl chloride diluted in 20 ml of 1,2-DCE are introduced dropwise with stirring and at −12° C. After returning to room temperature, the mixture is heated at the reflux temperature of the solvent for 1 hour. The mixture turns a brown colour. The volatile products are transferred under vacuum (10$^{-1}$ mm Hg) and trapped at −196° C. The solution obtained is colourless. A first, very slow distillation at atmospheric pressure allows the trimethylchlorosilane to be collected (b.p.:60° C., yield: 93%) and makes it possible to remove part of the DCE. The distillation is stopped when the residual volume is 50 ml. The distillation is completed with apparatus of the appropriate size. 4.8 g (yield: 17%) of the expected isocyanate are obtained, this product having the following characteristics:

Air-sensitive colourless liquid which turns yellow when it is stored at room temperature.

IR (CDCl$_3$):

2240 cm$^{-1}$ (NCO) strong band,
1700 cm$^{-1}$ (CO) strong band,
1645 cm$^{-1}$ (C=C) fine band.

We claim:

1. A process for the preparation of an acyl isocyanate wherein oxalyl chloride is reacted with a M-trialkylsilylcarboxamide or a N,N-bis(trialkylsilyl carboxamide.

2. The process according to claim 1 wherein said carboxamide has the formula:

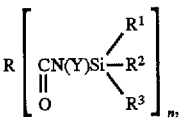

in which R is a C$_1$ to C$_{20}$, saturated or unsaturated, substituted or unsubstituted, linear or branched aliphatic radical;

a C$_4$ to C$_7$, saturated or unsaturated, substituted or unsubstituted cycloaliphatic radical, a substituted or unsubstituted phenyl, phenylene, naphthyl or naphthylene radical, a substituted or unsubstituted 5 or 6-membered, heteroaromatic radical, R$^1$, R$^2$ and R$^3$, are the same or different C$_1$ to C$_4$ alkyl radical, Y is a hydrogen atom or a group

in which R$^4$, R$^5$ and R$^6$, are the same or different C$_1$ to C$_4$ alkyl radical and n is 1 or 2.

3. The process according to claim 2 wherein R is a heteroaromatic radical containing at least one hetero atom which is a member selected from the group consisting of oxygen, nitrogen and sulphur.

4. The process according to claim 2 wherein R$^1$, R$^2$, R$^3$, R$^4$, R$^5$ and R$^6$ are a methyl radical.

5. The process according to claim 1 wherein the reaction is carried out in an inert organic solvent.

6. The process according to claim 5 wherein said solvent is a member selected from the group consisting of chlorinated or nonchlorinated aliphatic hydrocarbons, aromatic hydrocarbons and oxide ethers.

7. The process according to claim 6 wherein said solvent is a chlorinated aliphatic hydrocarbon.

8. The process according to claim 1 wherein the reaction temperature is between −15° C. and +120° C.

9. The process according to claim 8 wherein the oxalyl chloride to said carboxamide ratio is between 1 and 1.5.

10. The process according to claim 8 wherein the reaction is carried out in an inert organic solvent, said solvent having a reflux temperature, oxalyl chloride is dissolved in said solvent, the solution is cooled to between 0° and −12° C., then said carboxamide is added and after the addition of said carboxamide is complete, the reaction mixture is heated to the reflux temperature of said solvent.

11. The process according to claim 1 wherein said acyl isocyanate is a member selected from the group consisting of acetyl, trichloroacetyl, phenylacetyl, methacryloyl, 3-ethoxy- or 3-methoxyacryloyl, hexanoyl, palmitoyl, stearoyl, isobutyryl, pivaloyl, cinnamoyl, cyclopentanecarbonyl, cyclohexanecarbonyl, benzoyl, 2,6-difluorobenzoyl, o-methoxybenzoyl, 2,6-dichlorobenzoyl, nitrobenzoyl, naphthoyl, nicotinoyl, chloronicotinoyl, 5-nitrofuroyl, malonyl, succinyl, adipoyl, terephthaloyl and fumaryl isocyanate.

* * * * *